US006394947B1

(12) United States Patent
Leysieffer

(10) Patent No.: US 6,394,947 B1
(45) Date of Patent: May 28, 2002

(54) IMPLANTABLE HEARING AID WITH TINNITUS MASKER OR NOISER

(75) Inventor: Hans Leysieffer, Taufkirchen (DE)

(73) Assignee: Cochlear Limited, Lane Cove NSW (AU)

(*) Notice: Subject to any disclaimer, the term of this patent is extended or adjusted under 35 U.S.C. 154(b) by 0 days.

(21) Appl. No.: 09/468,860

(22) Filed: Dec. 21, 1999

(30) Foreign Application Priority Data

Dec. 21, 1998 (DE) ........................................ 198 59 171

(51) Int. Cl.[7] ........................ A04R 25/00; A61M 21/00; A61N 1/08

(52) U.S. Cl. ........................... 600/25; 600/28; 600/559; 607/57; 607/56; 607/55; 607/137

(58) Field of Search ............................ 600/25, 559, 28, 600/26, 27; 607/55, 56, 57, 136, 137; 381/68–69.2, 68.1, 68.2, 68.3, 68.4, 68.6; 181/129, 120, 134, 135; 623/10

(56) References Cited

U.S. PATENT DOCUMENTS

| | | | | |
|---|---|---|---|---|
| 4,532,930 | A | | 8/1985 | Crosby et al. |
| 4,741,339 | A | | 5/1988 | Harrison et al. |
| 5,015,225 | A | | 5/1991 | Hough et al. |
| 5,167,236 | A | * | 12/1992 | Junker ........................ 600/559 |
| 5,277,694 | A | | 1/1994 | Leysieffer et al. |
| 5,279,292 | A | | 1/1994 | Baumann et al. |
| 5,325,872 | A | * | 7/1994 | Westermann ............... 600/559 |
| 5,411,467 | A | | 5/1995 | Hortmann et al. |
| 5,554,096 | A | | 9/1996 | Ball |
| 5,624,376 | A | | 4/1997 | Ball et al. |
| 5,721,783 | A | | 2/1998 | Anderson |

(List continued on next page.)

FOREIGN PATENT DOCUMENTS

| | | | |
|---|---|---|---|
| DE | 39 40 632 | | 12/1990 |
| DE | 296 16 956 | U1 | 2/1997 |
| DE | 196 51 126 | A1 | 6/1998 |
| DE | 197 20 651 | A1 | 11/1998 |
| EP | 0 572 382 | B1 | 12/1993 |
| EP | 0 681 441 | A1 | 11/1995 |
| EP | 0 820 211 | A1 | 1/1998 |
| EP | 0 883 325 | A2 | 12/1998 |

OTHER PUBLICATIONS

Journal HNO 46: pp. 844–852, Oct. 1998, H.P. Zenner Et Al., Initial Implantation of a Completely Implantable Electronic Hearing System In Patients with An Inner Ear Hearing Disorder.

Journal HNO 46: pp. 853–863, Oct. 1998, Leysieffer Et Al., A Completely Implantable Hearing System For Inner Ear Hearing Handicapped: TICA LZ 3001.

WO 90/07251, Jun. 28, 1990, English Abstract.

Journal Hörakustik, 2/97, pp. 26 and 27, Tinnitus–Retraining–Therapie Und Hörakustik.

*Primary Examiner*—Kevin Shaver
*Assistant Examiner*—Navin Natnithithadha
(74) *Attorney, Agent, or Firm*—Nixon Peabody LLP; David S. Safran

(57) ABSTRACT

Partially or fully implantable hearing aid for rehabilitation of an inner ear hearing disorder, with a microphone (10) which delivers an audio signal, an electronic signal processing and amplification unit (40, 50, 80, 140, 141) which is located in an audio signal-processing electronic hearing aid path, an implantable electromechanical output converter (20) and a unit (60) for power supply of the implant. The hearing aid is provided with an electronic module (90, 140, 141) for rehabilitation of tinnitus and it generates the signals necessary for a tinnitus masking or noiser function and feeds them into the audio signal processing path of the hearing implant.

23 Claims, 5 Drawing Sheets

U.S. PATENT DOCUMENTS

| | | | | |
|---|---|---|---|---|
| 5,755,743 A | | 5/1998 | Volz et al. | |
| 5,788,711 A | | 8/1998 | Lenner et al. | |
| 5,795,287 A | | 8/1998 | Ball et al. | |
| 5,814,095 A | | 9/1998 | Müller et al. | |
| 5,941,814 A | | 8/1999 | Lehner et al. | |
| 6,048,305 A | * | 4/2000 | Bauman et al. | 600/25 |
| 6,068,590 A | * | 5/2000 | Brisken | 600/25 |
| 6,210,321 B1 | * | 4/2001 | Di Mino et al. | 600/28 |

* cited by examiner

IMPLANTABLE HEARING AID WITH TINNITUS MASKER OR NOISER

BACKGROUND OF THE INVENTION

1. Field of the Invention

The present invention relates to partially or fully implantable hearing aids for rehabilitation of an inner ear hearing disorder, which have a microphone which delivers an audio signal, an electronic signal processing and amplification unit which is located in an audio signal processing electronic hearing aid path, an implantable electromechanical output converter and a unit for supplying power to the hearing aid.

2. Description of Related Art

Partially and fully implantable hearing aids for rehabilitation of inner ear damage with mechanical stimulation of the damaged inner ear have recently been available or will soon be available on the market journal HNO 46:844-852, 10-1998, H. P. Zenner et al., "Initial implantations of a completely implantable electronic hearing system in patients with an inner ear hearing disorder"; journal HNO 46:853-863, 10-1998,. Leysieffer et al., "A completely implantable hearing system for inner ear hearing handicapped: TICA LZ 3001"); U.S. Pat. Nos. 5,277,694; 5,788,711; 5,814,095; 5,554,096; and 5,624,376.

Especially in filly implantable systems is the visibility of the system not an issue, so that in addition to the advantages of high sound quality, the open auditory canal and full suitability for everyday use, high future patient acceptance can be assumed.

Many individuals suffer from intermittent or permanent tinnitus which cannot be cured by surgery and against which there have been no approved drug forms of treatment to date. Therefore, so-called tinnitus maskers are known (published PCT application WO-A-90/07251). They are small, battery-operated devices which are worn like a hearing aid behind or in the ear and they cover (mask) the tinnitus psychoacoustically by artificial sounds which are emitted, for example, via a hearing aid speaker into the auditory canal and which reduce the disturbing tinnitus as far as possible below the threshold of perception. The artificial sounds are often narrowband noise (for example, third octave noise) which in its spectral position and its loudness level can be adjusted via a programming device to enable the maximum possible adaptation to the individual tinnitus situation. Moreover, there has recently been devised the so-called "retraining method" in which the perceptibility of the tinnitus is likewise supposed to be largely suppressed by a combination of a mental training program and presentation of broadband sound (noise) near the auditory threshold. These devices are also called "noisers" journal "Hoerakustik" 2/97, pages 26 and 27).

In the two aforementioned methods, technical devices similar to hearing aids can be visibly carried externally on the body in the area of the ear for treatment of tinnitus using hardware; they stigmatize the wearer and therefore are not willingly worn.

U.S. Pat. No. 5,795,287 discloses an implantable tinnitus masker with a direct driving of the middle ear, for example, via an electromechanical converter which is coupled to the ossicle chain. This directly coupled converter can preferably be a so-called "floating mass transducer" (FMT). This FMT corresponds to the converter for implantable hearing aids which is known from U.S. Pat. No. 5,624,376. U.S. Pat. No. 5,795,287 clearly describe especially the "direct drive" concept: this is defined explicitly as only the types of coupling to the inner ear for purposes of tinnitus masking which are of a mechanical nature, therefore direct mechanical converter couplings to one ossicle of the middle ear, such as, for example, by the FMT converter and also air gap-coupled electromagnetic converters such as is described, for example, in U.S. Pat. No. 5,105,225.

U.S. Pat. No. 5,795,287 describes solely implantable systems which are used for tinnitus masking and which are designed to mask the tinnitus based on direct mechanical stimulation of the inner ear with masking signal forms. But, since, as described above, inner ear noise very often occurs simultaneously with inoperable inner ear damage, for the wearer of the implant known from U.S. Pat. No. 5,795,287, technical and hardware measures must also be taken to rehabilitate the inner ear damage. This is only possible by additional application of a hearing aid of conventional design, i.e. a hearing aid worn outside on the body with acoustic stimulation of the eardrum. Especially here, neither a partially nor a fully implantable system is considered, since these systems, likewise, require mechanical coupling to a suitable middle ear structure for mechanical stimulation of the inner ear; one such simultaneous application of two different implants which must fundamentally deliver their actuator stimulus at the same destination is hardly feasible either surgically or technically; in addition, it entails other major clinical risks.

SUMMARY OF THE INVENTION

A primary object of this invention is to treat more easily and effectively the problems associated with the simultaneous occurrence of inner ear damage and tinnitus while avoiding the above described defects.

Proceeding from a partially or fully implantable hearing aid for rehabilitation of a inner ear hearing disorder with a microphone which delivers an audio signal, with an electronic signal processing and amplification unit which is located in an audio signal-processing electronic hearing aid path, with an implantable electromechanical output converter and with a unit for power supply of the implant, this object is achieved in accordance with the invention by the hearing aid for rehabilitation of tinnitus being provided with an electronic module which generates the signals necessary for tinnitus masking, or for a noiser function, and feeds them into the audio signal processing path of the hearing implant.

The hearing aid of the invention makes it possible, using a single active, at least partially implantable system, to treat not only inner ear damage, but also and at the same time, tinnitus. Stigmatization of the patient by visible external hearing aid parts is kept small in the case of a partially implantable simultaneous therapy system, and it is completed avoided in a fully implantable device. The surgery necessary for at least partial implantation of the combination device and the associated residual risks do not exceed what must be tolerated anyway in an at least partially implantable hearing aid alone or in an at least partially implantable tinnitus masker alone.

As the implantable electromechanical output converter especially a converter as per U.S. Pat. No. 5,277,694 is suitable, i.e. a converter in which one wall of the converter housing is made as a vibratory membrane which together with a piezoelectric ceramic wafer applied to the inside of the membrane represents an electromechanically active heteromorphic composite element.

Another converter design suitable for these purposes is described in the co-pending, commonly owned U.S. patent application Ser. No. 09/275,872. It is a converter arrangement for partially or fully implantable hearing aids for direct mechanical excitation of the middle ear or inner ear, which is provided with a housing which can be fixed at the implantation site with respect to the skull and with a mechanically stiff coupling element which can move relative to the housing, the housing containing an electromechanical converter with which the coupling element can be caused to vibrate; these vibrations are transmitted to the middle ear ossicle or directly to the inner ear after completed implantation of the converter arrangement. The electromechanical converter is made as an electromagnet arrangement which has a component which is fixed relative to the converter housing, especially a ring coil, and a vibratory component, preferably in the form of a permanent magnetic pin which dips into the center opening of the ring coil and which is connected to the coupling element such that the vibrations of the vibratory component are transmitted to the coupling element.

However, a converter of the type described in the co-pending, commonly owned U.S. patent application Ser. No. 09/311,563 is also advantageous. It is a converter for partially or fully implantable hearing aids for direct mechanical excitation of the middle ear or inner ear which is provided with a housing which can be fixed at the implantation site and with a mechanically stiff coupling element which can move relative to the housing, the housing containing a piezoelectric element with which the coupling element can be caused to vibrate; these vibrations are transmitted to the middle ear ossicle or directly to the inner ear after completed implantation of the converter, and in the housing, there being an electromagnet arrangement which has a component which is fixed relative to the housing and has a vibratory component which is connected to the coupling element such that the vibrations of the vibratory component are transmitted to the coupling element. This converter has the advantage that the frequency response of the converter can be improved compared to both purely piezoelectric and purely electromagnetic systems, so that an adequate hearing impression at a sufficient loudness level is enabled. In particular, a largely flat frequency response of the deflection of the coupling element can be implemented in a wide frequency band at a sufficiently high stimulation level and low power consumption.

In the hearing aid according to the invention, preferably patient-specific signal parameters for tinnitus masking or the noiser function can be individually adapted to the requirements and pathological demands of the patient by means of an electronic unit.

The electronic signal processing and amplification unit can have an amplifier connected downstream of the microphone, an audiological signal processing stage supplied with the output signal of the amplifier and a driver amplifier connected upstream of the electromechanical output converter. Advantageously, the electronic module can be provided with a signal generator arrangement for generating the signals necessary for tinnitus masking or the noiser function, and a summing element connected between the signal processing stage and the driver amplifier, via which both the output signal of the audiological signal processing stage and also the output signal of the signal generator arrangement pass to the driver amplifier.

However, according to a modified embodiment of the invention, there can also be a digital signal processor as the audiological signal processing stage which is designed both for conditioning of the audio signal and also for generating the signals necessary for tinnitus masking or the noiser function and for combining the latter signals with the audio signal. In this case, an analog to digital converter can be connected upstream and a digital to analog converter downstream of the signal processor. The digital to analog converter and the driver amplifier can be combined in one module.

The signal processor is preferably equipped with a data storage for storing the patient-specific, audiological adaptation parameters and/or parameters for generating the signals for tinnitus masking or the noiser function.

To control at least one part, and preferably all of the signal processing and/or signal generating stages, there can advantageously be a microcontroller which has a data store for storing patient-specific, audiological adaptation parameters and/or the operating parameters of the signal generator arrangement.

However, the signal processor can also be designed itself for controlling at least a part and preferably all of the signal processing and/or signal generating stages.

For data input into the data store, a telemetry unit is suitable which communicates by wire or wirelessly with an external programming system.

If the hearing aid is made to be fully implantable, preferably the signal processing and amplification unit which is in the electronic hearing aid path, the electronic module for generating and feeding the signals necessary for tinnitus masking or the noiser function and the telemetry unit as the electronic module are housed together with the power supply unit in a hermetically sealed and biocompatible implant housing. Here, the electronic module is advantageously connected via an implant line to a microphone which can be implanted subcutaneously in the rear wall of the auditory canal and via an implantable line to the electromechanical output converter. This connection can be made permanent or detachable. For a detachable connection, especially a plug-in connection as is described in particular in U.S. Pat. 5,755,743 is suitable. One such connection arrangement has at least a first contact, at least one second contact supported on an elastic body and a sealing mechanism for causing the face of the first contact to engage the face of the second contact, the first contact being surrounded by at least one sealing crosspiece which is pressed into the elastic body when the contacts engage and which seals the contacts to the outside.

The output converter can be coupled, preferably via a coupling element, to an ossicle of the middle ear chain for transmission of the output-side mechanical converter vibrations. Especially the approaches of the type described in U.S. Pat. Nos. 5,277,694 and 5,941,814 are suitable for this purpose. Here, advantageously, an actively vibratory part of the output converter can be joined mechanically securely to a connecting rod which is coupled via a coupling element to part of the ossicle chain. To adjust the relative location of the connecting rod and coupling element and to fix these elements in the adjusted relative position, the coupling element is preferably made sleeve-shaped, at least in the fixing area, and it can be plastically cold-deformed by means of a crimping tool, while the connecting rod is made bar-shaped, at least in the fixing area, is provided with a rough surface, and under the influence of the crimping force applied with the crimping tool, it cannot be plastically cold-deformed, in the fixed state the sleeve-shaped part of the coupling element deformed by cold flow by the crimping force being attached permanently and without play on the bar-shaped part of the connecting rod. The end of the connecting rod which is at a distance from the output converter, however, can also be inserted into a hole of one part of the ossicle chain and fixed there.

Furthermore, the output converter can also be designed such that it can be coupled via an air gap to the ossicle chain or to the inner ear, as is described in particular in U.S. Pat. No. 5,015,225.

A fully implantable hearing aid, in another embodiment of the invention, includes an external system for transcutaneous transfer of patient-specific hearing aid and tinnitus masking or noiser programming data to the implant-side telemetry unit.

As the power supply unit, in particular a primary battery or a secondary, rechargeable element, i.e., a rechargeable battery, can be considered. In the latter case, the telemetry unit is additionally made preferably as a power receiving circuit for implant-side availability of recharging energy for the power supply unit, while the external system is, at the same time, built as a charger. In particular, a charging system of the type known from U.S. Pat. No. 5,279,292 or arrangements of the type that are described in commonly-owned, co-pending U.S. patent application Ser. Nos. 09/311,565 and 09/311566 are suitable for this purpose.

It is also possible to provide a portable remote control unit for setting or changing the hearing aid and tinnitus masking or noiser functions.

In a partially implantable system, an implant part preferably has, in addition to the output converter, a power and signal receiving interface and an electronic system connected between the receiving interface and the output converter, with the components necessary for power supply and data regeneration, and the external system part comprises the microphone, an electronic module with the signal processing unit in the hearing aid path and with the electronic module which is necessary for generation and feed of the signals necessary for tinnitus masking or the noiser function, a driver unit, and a power and signal transmitting interface connected to the output of the driver unit.

Furthermore, the partially implantable hearing aid includes, preferably, an external system for transfer of patient-specific hearing aid and tinnitus masking or noiser function programming data to the electronic module of the external system part.

In the following, advantageous embodiments of the invention are explained in conjunction with the accompanying drawings.

DETAILED DESCRIPTION OF THE INVENTION

Figure 1:
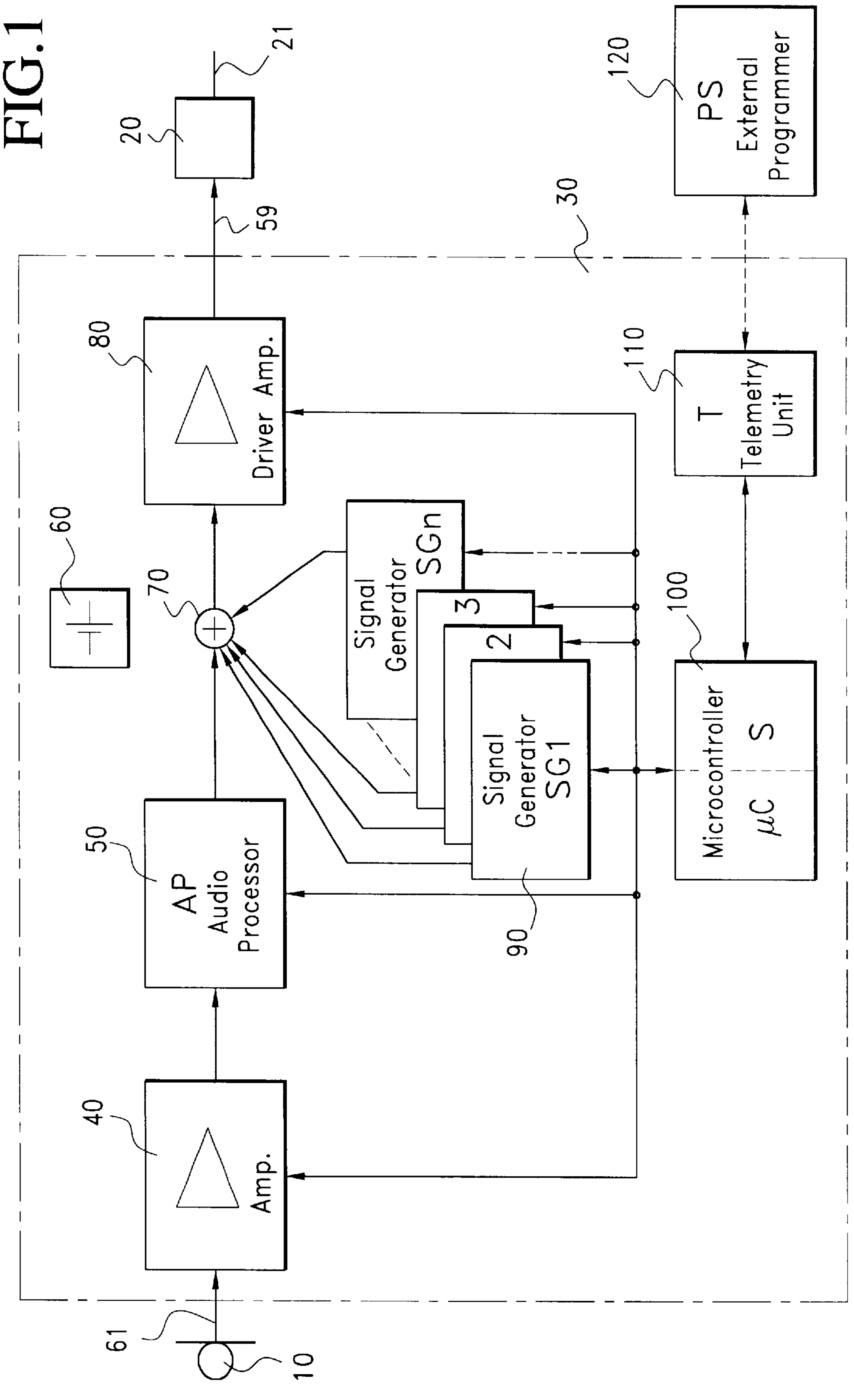
FIG. 1 shows a block diagram of a fully implantable hearing aid according to the invention.

The implant system as shown in FIG. 1 has a microphone 10 which receives the acoustic signal and converts it into an electrical signal which is pre-amplified in an amplifier 40. This pre-amplified signal is further processed in an audiological signal processing stage 50 ("Audio Processor"). This stage can contain all known components which are conventional in modern hearing aids, such as filter stages, automatic gain controls, interference signal suppression means and so forth. This processed signal is sent to a summation element 70.

Further inputs of the summation element 70 are the output or outputs of one or more signal generators 90 (SG1 to SGn) which generate(s) the signal or signals which are necessary for tinnitus masking or the noiser function. In the conventional manner, they can be individual sinusoidal signals, narrowband signals, broadband signals and the like, with a spectral location, level and phase ratios which can be adjusted to one another.

The audio signal processed by the stage 50 together with the masker or noiser signal or signals of the generator or generators 90 is sent to a driver amplifier 80 which triggers an electromechanical converter 20. The converter 20 stimulates the damaged inner ear by direct mechanical coupling via the coupling element 21 to a middle ear ossicle or via air gap coupling for implantable converters which are electromagnetic, for example. The signal processing components 40, 50, 80 and the generators 90 are controlled by a microcontroller 100 ($\mu$C) with the pertinent data storage (S). In the storage area S, especially patient-specific audiological adaptation parameters and the individual operating parameters of the signal generator 90 for tinnitus masking or the noiser function can be filed. These individual programmable data are sent to the controller 100 via a telemetry unit 110 (T). This telemetry unit 110 communicates wirelessly or by wire bidirectionally with an external programming systems 120 (PS).

All electronic components of the system except for the programming system 120 are supplied with electrical operating power by a primary or rechargeable secondary battery 60.

In particular, in a fully implantable system, it is a good idea to combine all the described electronic signal processing circuit parts and the control components and the power supply in a single signal module 30; this is shown in FIG. 1 by the dot-dash line. On the implant side only, the microphone 10 and the electromechanical converter 20 are connected to this signal module 30 via the corresponding lines 61 or 59, permanently or optionally via implantable plug-in connections.

Figure 2:
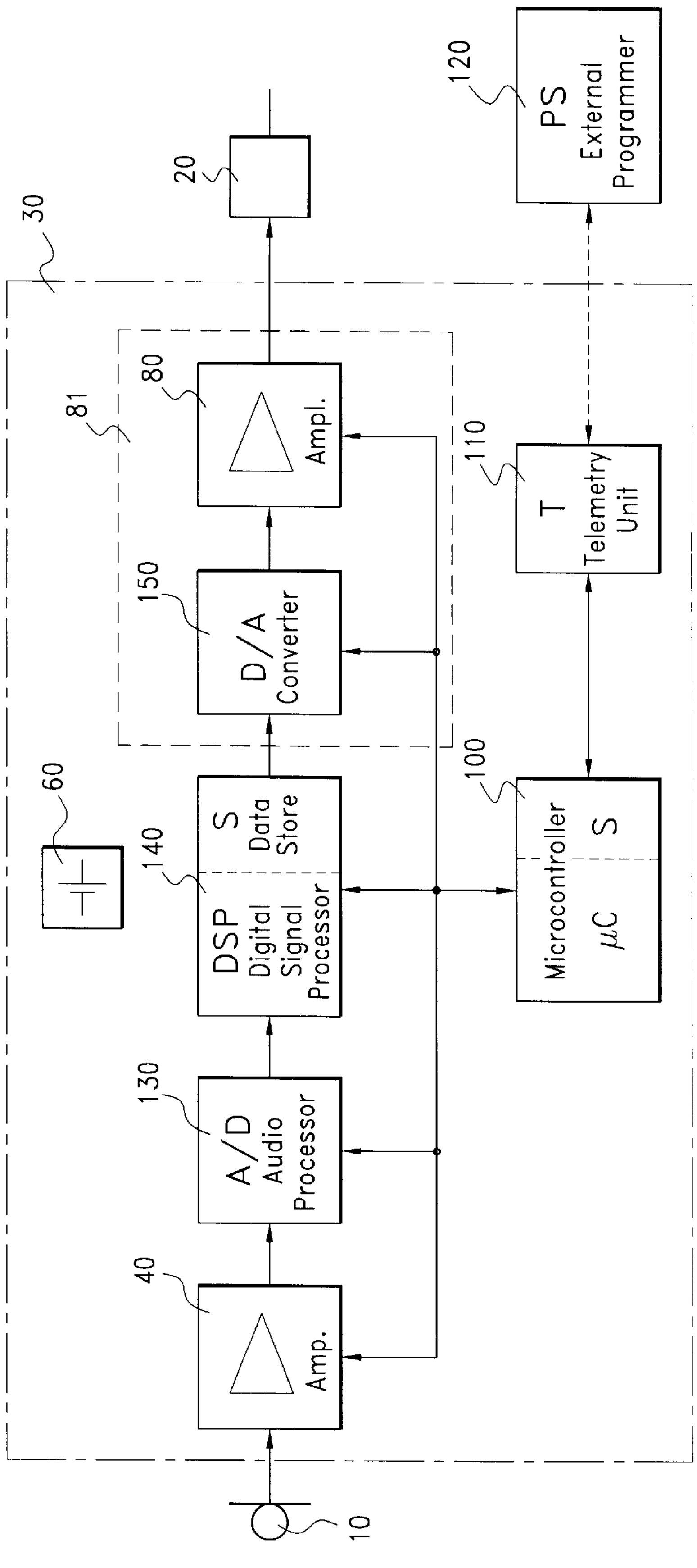
FIGS. 2 & 3 each shows a block diagram of a modified embodiment of a fully implantable hearing aid.

FIG. 2 shows another embodiment of the electronic signal module 30. The signal of the microphone 10 is pre-amplified in the amplifier 40 and by means of an analog-digital converter 130 (A/D) is converted into a digital signal which is sent to a digital signal processor 140 (DSP) with a data storage area S. The signal processor 140 assumes fundamentally two tasks: on the one hand, as in fully digital hearing aids, the audio signal is conventionally processed according to the described signal processing methods for rehabilitation of inner ear damage. On the other hand, in the signal processor 140, the signal generators which generate the signals necessary for tinnitus masking or achieving the noiser function are implemented using hardware or software. The combination of these digital masker or noiser signals and the processed and amplified audio signal take place, likewise, in the signal processor 140. The digital output signal of the signal processor 140 is converted back in a digital-analog converter 150 (D/A) into an analog signal and is sent to the electromechanical converter 20 via the driver amplifier 80.

The D/A converter 150 and the driver amplifier 80, as is shown in FIG. 2 by the block 81, can be combined in one module. This is especially preferred in the case in which an electromagnetic system is used as the converter 20 and the output signal of the signal processor 140 contains the signal information by pulse-width modulation so that the time integration necessary for conversion back into an analog signal is performed directly by the converter 20.

All signal processing components are controlled by a microcontroller 100 ($\mu$C) with the pertinent data storage (S). The storage area S of the microcontroller 100 can file especially patient-specific audiological adaptation parameters and the individual operating parameters of the signal generators for tinnitus masking or the noiser function which are integrated into the signal processor 140. These individual programmable data are sent to the controller 100 via a telemetry unit 110 (T). This telemetry unit 110 communicates wirelessly or by wire bidirectionally with an external programming systems 120 (PS). All electronic components of the system, except for the programming system 120, are supplied with electrical operating power by the primary or secondary battery 60.

Figure 3:
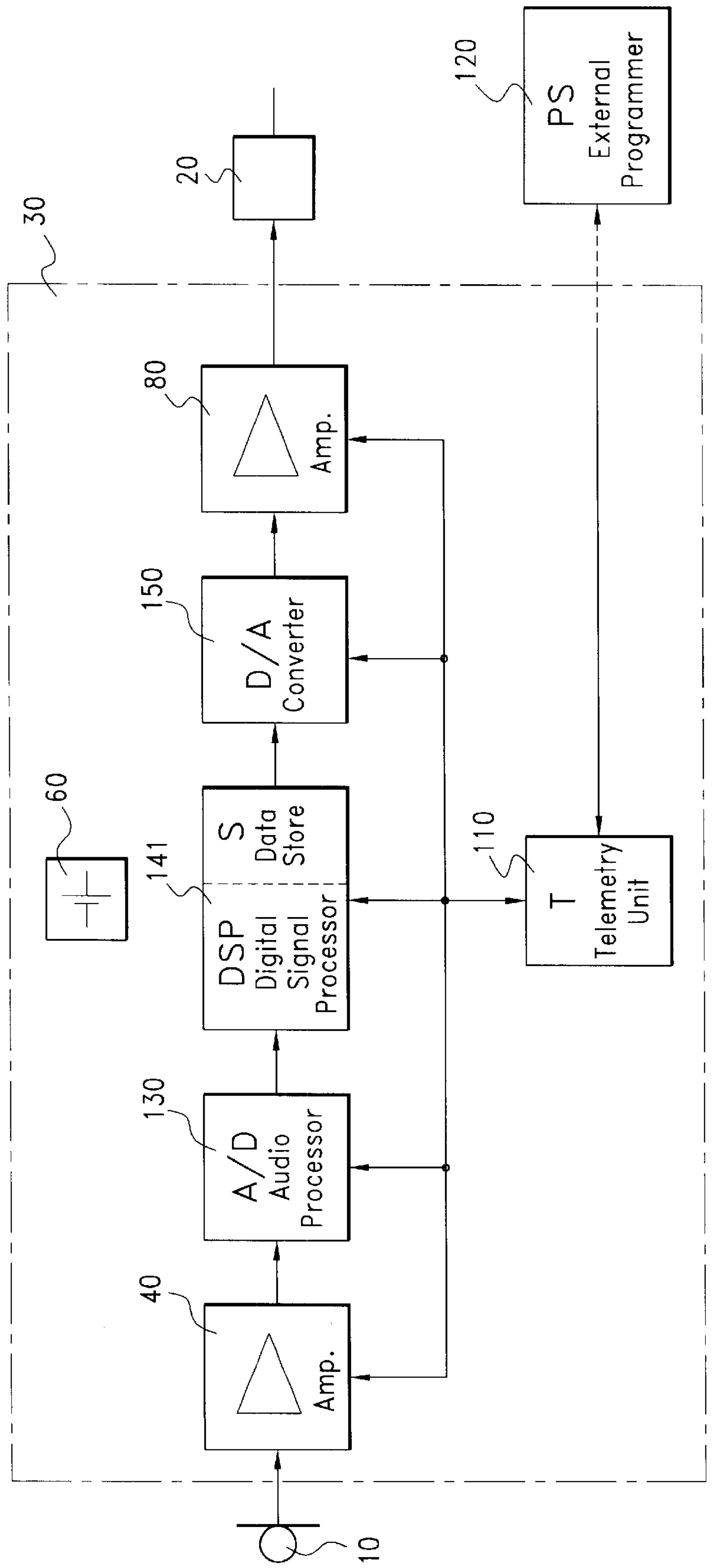

The embodiment as shown in FIG. 3 differs from that of FIG. 2 essentially only in that there is a signal processor 141 which also assumes the functions of the microcontroller 100 as shown in FIG. 2. Here, the patient-specific data of audio signal processing and the tinnitus masking or the noiser functions are then likewise filed in the data storage area S of the signal processor 141.

Figure 4:
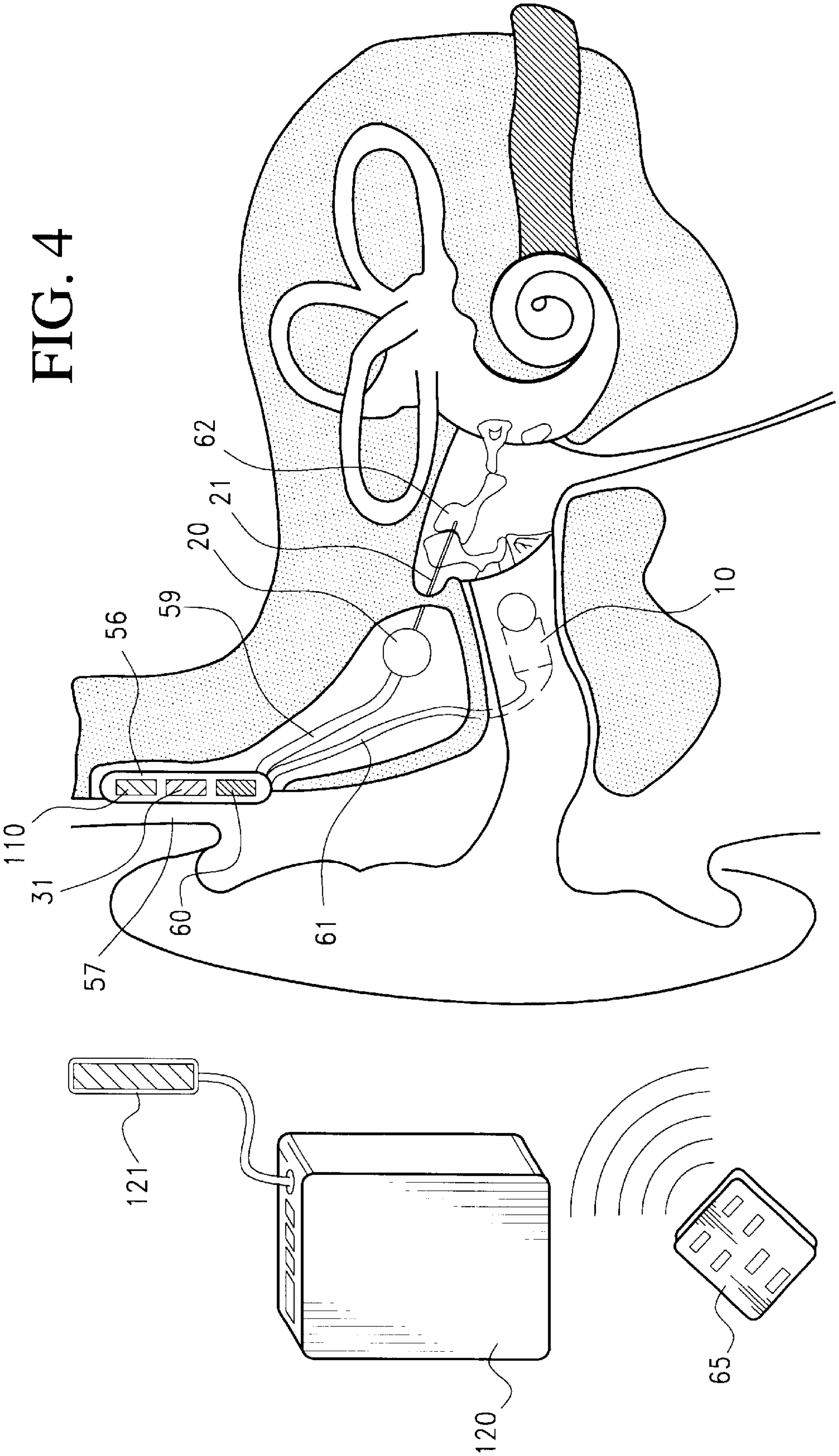
FIG. 4 is a schematic diagram of a filly implantable hearing aid in the implanted state.

FIG. 4 shows, in schematic form, one possible fully implantable embodiment using the hearing aide as shown in FIGS. 1, 2 or 3. A hermetically tight and biocompatible implant housing 56 holds an electronic module 31 (shown without the battery) which corresponds to the module 30 of FIGS. 1, 2, and 3 except for the absence of a battery. Furthermore, the housing 56 contains the battery 60 for electrical supply of the implant and the telemetry means 110. The microphone 10 is subcutaneously implanted preferably in the manner known from U.S. Pat. No. 5,814,095, optionally in the rear wall of the auditory canal using the fixation element described in commonly owned, co-pending U.S. patent application Ser. No. 09/097,710. The microphone 10 receives the sound and converts it into an electrical signal which is supplied via the implant line 61 to the electronic module 31 in the housing 56. The audiologically processed and amplified signal to which the corresponding tinnitus masking or the noiser signals are added by the electronic unit 31 travels via the implantable line 59 to the electromechanical converter 20. This converter 20, in this example, is shown as a directly coupled system, i.e., the output-side mechanical vibrations of the converter 20 are coupled directly via a suitable coupling element 21 to an ossicle of the middle ear chain, in this case to the incus 62. Preferably, this takes place in the manner known from U.S. Pat. Nos. 5,277 694 and 5,788,711. The converter vibrations coupled in there travel via the ossicle chain to the inner ear, and there, cause the corresponding auditory impression.

Furthermore, FIG. 4 shows the external programming system 120 with which, as described, the patient-specific hearing aid and tinnitus masker or the noiser data are transferred transcutaneously through the closed skin 57 to the implant-side telemetry unit 110. To do this, a transmitting head 121 is used which is placed above the implant for (bidirectional) data transfer and transfers the data, for example, inductively. If the battery 60 in the implant housing 56 is a secondary, rechargeable element, the unit 110 can also be a power receiving circuit for implant-side availability of recharging energy. Then, the external system 120 with the transmitting head. 121 is a wireless charger which is portable, for example. Here preferably, there can be arrangements as are known from U.S. Pat. No. 5,279,292 or as are explained in the above-mentioned U.S. patent application Ser. Nos. 09/311,565, and 09/311,566. Furthermore, a portable remote control unit 65 is shown with which the patient can adjust or change important hearing aid and tinnitus masker or noiser functions.

Figure 5:
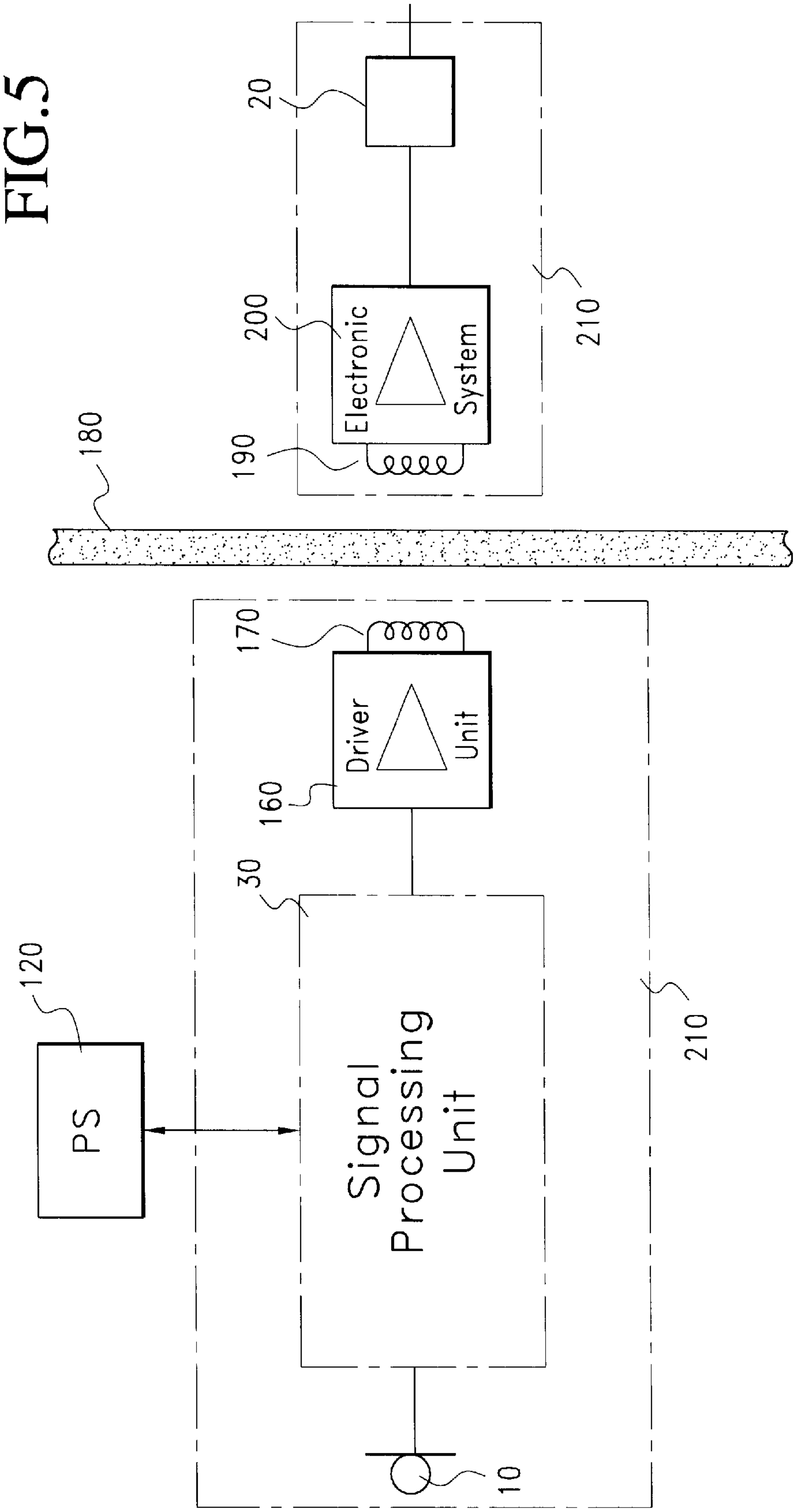
FIG. 5 shows a block diagram of a partially implantable hearing aid in accordance with the invention.

FIG. 5 schematically shows a partially implantable system. Here, the implantable part is shown as the subsystem 220 and the external part which is to be worn outside on the body is shown as the block 210. The external unit 210 contains the microphone 10, a signal processing unit 30 and the driver unit 160 which transfers the generated signals and operating power for the implant part, for example, via the transmitting coil 170 inductively and transcutaneously through the closed skin 180 to the implanted system part 220. This type of transmission corresponds to transmission in known, partially implantable cochlea implants or partially implantable hearing aids or partially implantable tinnitus maskers (see among others U.S. Pat. No. 4,741,339, published European Patent Application 0 572 382 B, and U.S. Pat. No. 5,795,287). The electronic unit 30 of the external system part 210 contains all necessary electronic components for hearing aid signal processing and for tinnitus masking or the noiser function are explained, for example, using FIGS. 1 to 3. The individual programming of the external system with patient-specific hearing aid and tinnitus masking or noiser data takes place via the programming system 120 which as in conventional hearing aids is conventionally coupled, in this case by wire, to the electronic unit 30. The implant-side the system 220 comprises a power and signal receiving interface, in this case an inductive receiving coil 190. The electronic system 200 contains all components necessary for power supply and data regeneration, such as demodulators and driver circuits for the electromechanical converter 20.

While various embodiments in accordance with the present invention have been shown and described, it is understood that the invention is not limited thereto, and is susceptible to numerous changes and modifications as known to those skilled in the art. Therefore, this invention is not limited to the details shown and described herein, and includes all such changes and modifications as are encompassed by the scope of the appended claims.

What is claimed is:

1. An at least partially implantable hearing aid for rehabilitation of an inner ear hearing disorder comprising a microphone which outputs an audio signal, an implantable electromechanical output converter for direct mechanical inner ear stimulation via a coupling element, an electronic signal processing and amplification unit which is located in an audio signal processing electronic hearing aid path from the microphone to the implantable electromechanical output converter and which receives said audio signal, a power unit for electrically powering the hearing aid, and an electronic module for rehabilitation of tinnitus which generates tinnitus masking or noiser signals and feeds them into said audio signal processing path in a manner driving said electromechanical output converter.

2. Hearing aid as claimed in claim 1, wherein the electronic unit has means for adapting the signals generated thereby to patient-specific signal parameters meeting requirements for tinnitus masking or noiser function requirements of various individual patients.

3. Hearing aid as claimed in claim 2, wherein the electronic signal processing and amplification unit comprises an amplifier, an audiological signal processing stage which is connected to receive an output signal of the amplifier and a driver amplifier which is connected upstream of the electromechanical output converter.

4. Hearing aid as claimed in claim 3, wherein the electronic module further comprises a signal generator arrangement for generating the tinnitus masking or noiser signals and a summing element connected between the signal processing stage and the driver amplifier, via which both the output signal of the audiological signal processing stage and the signals of the signal generator arrangement pass to the driver amplifier.

5. Hearing aid as claimed in claim 3, wherein the audiological signal processing stage is a digital signal processor which both conditions the audio signal and generates the tinnitus masking or noiser signals and combines the tinnitus masking or noiser signals with the audio signal.

6. Hearing aid as claimed in claim 5, wherein an analog to digital converter is connected upstream of the signal processor and a digital to analog converter is connected downstream of the signal processor.

7. Hearing aid as claimed in claim 6, wherein the digital to analog converter and the driver amplifier are combined in a single module.

8. Hearing aid as claimed in claim 5, wherein the signal processor has a data storage for storing at least one of the patient-specific parameters and parameters for generating the tinnitus masking or noiser signals.

9. Hearing aid as claimed in claim 3, wherein at least part of the audiological signal processing stage is controlled by a microcontroller.

10. Hearing aid as claimed in claim 9, wherein the microcontroller has a data storage for storing the patient-specific signal parameters.

11. Hearing aid as claimed in claim 5, wherein the signal processor itself comprises a microcontroller with a data storage for storing at least one of the patient-specific parameters and parameters for generating the tinnitus masking or noiser signals.

12. Hearing aid as claimed in claim 8, wherein a telemetry unit is provided for inputting data into the data storage.

13. Hearing aid as claimed in claim 12, further comprising an external programming system which communicates with the telemetry unit.

14. Hearing aid as claimed in claim 12, wherein the hearing aid is fully implantable, the signal processing and amplification unit, the electronic module and the telemetry unit being housed together with the power supply unit in a hermetically sealed, biocompatible implant housing.

15. Hearing aid as claimed in claim 14, wherein the electronic module is connected via an implant line to the microphone which is subcutaneously implantable in a rear wall of an auditory canal.

16. Hearing aid as claimed in claim 15, wherein the electronic module is connected via an implantable line to the electromechanical output converter.

17. Hearing aid as claimed claim 1, wherein the output converter is coupled to a coupling element for transmission of output-side mechanical converter vibrations to an ossicle of the middle ear chain.

18. Hearing aid as claimed in claim 1, wherein the output converter is coupleable to the ossicle chain or the inner ear via an air gap.

19. Hearing aid as claimed in claim 14, further comprising an external system for transcutaneous transfer of patient-specific hearing aid and tinnitus masking or noiser programming data to the telemetry unit.

20. Hearing aid as claimed in claim 19, wherein the power supply unit is a secondary, rechargeable element, the telemetry unit is additionally a power receiving circuit for implant-side availability of recharging energy for the power supply unit, and wherein the external system is also a charger for the power supply unit.

21. Hearing aid as claimed in claim 14, further comprising a portable remote control unit for adjusting or changing the hearing aid and tinnitus masking or noiser functions thereof.

22. Hearing aid as claimed in claim 1, wherein the hearing is partially implantable, having an implant part comprising the output converter, a power and signal receiving interface and an electronic system which is connected between the receiving interface and the output converter with components necessary for power supply and data regeneration, and an external system part comprising the microphone, a signal processing module with the signal processing and amplification unit, said electronic module, a driver unit and a power and signal transmitting interface connected to an output of the driver unit.

23. Hearing aid as claimed in claim 22, further comprising an external system for transfer of patient-specific hearing aid and tinnitus masker or noiser programming data to the electronic module of the external system part.

* * * * *